US007858055B2

(12) United States Patent
Lee et al.

(10) Patent No.: US 7,858,055 B2
(45) Date of Patent: Dec. 28, 2010

(54) MOISTURE SENSITIVE AUXETIC MATERIAL

(75) Inventors: WanDuk Lee, Seoul (KR); SangSoo Lee, Yongin-si (KR); CholWoh Koh, Suwon-si (KR); Jin Heo, Yongln-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/337,821

(22) Filed: Dec. 18, 2008

(65) Prior Publication Data

US 2010/0159768 A1 Jun. 24, 2010

(51) Int. Cl.
 *D03D 15/00* (2006.01)
(52) U.S. Cl. ....................................................... 422/199
(58) Field of Classification Search ................. 442/199, 442/200, 201, 202
 See application file for complete search history.

(56) References Cited

U.S. PATENT DOCUMENTS

| | | | |
|---|---|---|---|
| 2,681,032 A | 6/1954 | Shaw |
| 3,338,992 A | 8/1967 | Kinney |
| 3,341,394 A | 9/1967 | Kinney |
| 3,371,668 A | 3/1968 | Johnson |
| 3,502,538 A | 3/1970 | Petersen |
| 3,502,763 A | 3/1970 | Hartmann |
| 3,542,615 A | 11/1970 | Dobo et al. |
| 3,556,932 A | 1/1971 | Coscia et al. |
| 3,556,933 A | 1/1971 | Williams et al. |
| 3,692,618 A | 9/1972 | Dorschner et al. |
| 3,802,817 A | 4/1974 | Matsuki et al. |
| 3,849,241 A | 11/1974 | Butin et al. |
| 4,246,900 A | 1/1981 | Schroder |
| 4,340,563 A | 7/1982 | Appel et al. |
| 4,357,938 A | 11/1982 | Ito et al. |
| 4,447,240 A | 5/1984 | Ito et al. |
| 4,488,928 A | 12/1984 | Ali Khan et al. |
| 4,623,342 A | 11/1986 | Ito et al. |
| 4,640,859 A | 2/1987 | Hansen et al. |
| 4,675,394 A | 6/1987 | Solarek et al. |
| 4,779,456 A | 10/1988 | Cantoni |
| 4,781,731 A | 11/1988 | Schlinger |
| 4,787,896 A | 11/1988 | Houghton et al. |
| 4,809,493 A | 3/1989 | Genba et al. |
| 4,834,733 A | 5/1989 | Huntoon et al. |
| 4,981,557 A | 1/1991 | Bjorkquist |
| 5,007,906 A | 4/1991 | Osborn, III et al. |
| 5,008,344 A | 4/1991 | Bjorkquist |
| 5,085,736 A | 2/1992 | Bjorkquist |
| 5,176,672 A | 1/1993 | Bruemmer et al. |
| 5,181,563 A | 1/1993 | Amaral |
| 5,260,345 A | 11/1993 | Desmarais et al. |
| 5,334,176 A | 8/1994 | Buenger et al. |
| 5,397,316 A | 3/1995 | Lavon et al. |
| 5,415,640 A | 5/1995 | Kirby et al. |
| 5,447,507 A | 9/1995 | Yamamoto |
| 5,514,121 A | 5/1996 | Roe et al. |
| 5,520,674 A | 5/1996 | Lavon et al. |
| 5,527,303 A | 6/1996 | Milby, Jr. et al. |
| 5,575,785 A | 11/1996 | Gryskiewicz et al. |
| 5,591,150 A | 1/1997 | Olsen et al. |
| 5,779,860 A | 7/1998 | Hollenberg et al. |
| 5,833,680 A | 11/1998 | Hartman |
| 5,858,515 A | 1/1999 | Stokes et al. |
| 5,997,520 A | 12/1999 | Ahr et al. |
| 6,045,900 A | 4/2000 | Haffner et al. |
| 6,071,580 A | 6/2000 | Bland et al. |
| 6,114,597 A | 9/2000 | Romare |
| 6,133,501 A | 10/2000 | Hallock et al. |
| 6,168,583 B1 | 1/2001 | Tanji et al. |
| 6,175,056 B1 | 1/2001 | Carlucci et al. |
| D448,476 S | 9/2001 | Page et al. |
| 6,293,935 B1 | 9/2001 | Kimura et al. |
| D448,846 S | 10/2001 | Page et al. |
| 6,296,628 B1 | 10/2001 | Mizutani |
| 6,306,818 B1 | 10/2001 | Anderson et al. |
| 6,315,765 B1 | 11/2001 | Datta et al. |
| 6,326,525 B1 | 12/2001 | Hamajima et al. |
| 6,346,097 B1 | 2/2002 | Blaney |
| 6,348,047 B1 | 2/2002 | Harper |
| 6,387,084 B1 | 5/2002 | VanGompel et al. |
| 6,392,117 B1 | 5/2002 | Mayer et al. |
| 6,429,261 B1 | 8/2002 | Lang et al. |
| 6,432,097 B1 | 8/2002 | Ahr et al. |
| 6,436,081 B1 | 8/2002 | Wada et al. |
| 6,444,214 B1 | 9/2002 | Cole et al. |
| 6,521,811 B1 | 2/2003 | Lassen et al. |
| 6,537,663 B1 | 3/2003 | Chang et al. |
| 6,548,592 B1 | 4/2003 | Lang et al. |
| 6,551,297 B2 | 4/2003 | Tanaka et al. |
| 6,579,570 B1 | 6/2003 | Lang et al. |

(Continued)

FOREIGN PATENT DOCUMENTS

CN D 3251084 8/2002

(Continued)

*Primary Examiner*—Arti Singh-Pandey
(74) *Attorney, Agent, or Firm*—Denise L. Stoker

(57) ABSTRACT

An auxetic fiber and corresponding material that not only responds to an external force, but also responds to moisture. The auxetic fiber is made in part from a moisture activated shrinking filament. Even if no external force is applied to the fiber, a pseudo tensile force is created by wetting the auxetic fiber.

16 Claims, 3 Drawing Sheets

U.S. PATENT DOCUMENTS

| | | | |
|---|---|---|---|
| 6,585,712 B2 | 7/2003 | Yoshimasa | |
| 6,599,848 B1 | 7/2003 | Chen et al. | |
| 6,620,144 B1 | 9/2003 | Glasgow et al. | |
| 6,627,670 B2 | 9/2003 | Mork et al. | |
| 6,632,205 B1 | 10/2003 | Sauer | |
| 6,653,406 B1 | 11/2003 | Soerens et al. | |
| 6,664,436 B2 | 12/2003 | Topolkaraev et al. | |
| 6,666,850 B1 | 12/2003 | Ahr et al. | |
| 6,683,143 B1 | 1/2004 | Mumick et al. | |
| 6,713,414 B1 | 3/2004 | Pomplun et al. | |
| 6,727,004 B2 | 4/2004 | Goulet et al. | |
| 6,786,893 B2 | 9/2004 | Strand | |
| 6,815,502 B1 | 11/2004 | Lang et al. | |
| 6,840,925 B2 | 1/2005 | Mishima et al. | |
| 6,908,458 B1 | 6/2005 | Sauer et al. | |
| 6,958,430 B1 | 10/2005 | Marinelli | |
| D521,149 S | 5/2006 | Adams et al. | |
| 7,037,298 B2 | 5/2006 | Ohshima et al. | |
| 7,145,054 B2 | 12/2006 | Zander et al. | |
| 7,179,247 B2 | 2/2007 | Mizutani et al. | |
| 7,252,870 B2 | 8/2007 | Anderson et al. | |
| 7,314,967 B2 | 1/2008 | Ashton et al. | |
| D567,369 S | 4/2008 | Gilroy | |
| 7,358,282 B2 | 4/2008 | Krueger et al. | |
| 7,491,864 B2 | 2/2009 | Nishizawa et al. | |
| D600,802 S | 9/2009 | Hood et al. | |
| D600,803 S | 9/2009 | Hood et al. | |
| D600,805 S | 9/2009 | Hood et al. | |
| 7,621,899 B2 | 11/2009 | Fujikawa et al. | |
| 2001/0029359 A1 | 10/2001 | Carlucci | |
| 2003/0050614 A1 | 3/2003 | D'Acchioli et al. | |
| 2005/0010185 A1 | 1/2005 | Mizutani et al. | |
| 2006/0116651 A1 | 6/2006 | Kurita et al. | |
| 2006/0148917 A1 | 7/2006 | Radwanski et al. | |
| 2006/0246272 A1 | 11/2006 | Zhang et al. | |
| 2006/0282059 A1 | 12/2006 | Fujikawa et al. | |
| 2006/0287635 A1 | 12/2006 | Angel | |
| 2007/0031667 A1* | 2/2007 | Hook et al. | 428/373 |
| 2007/0043027 A1 | 2/2007 | Rueckle et al. | |
| 2007/0210011 A1* | 9/2007 | Hook | 210/767 |
| 2007/0225671 A1 | 9/2007 | Angel | |
| 2007/0287973 A1 | 12/2007 | Cohen et al. | |
| 2008/0269703 A1 | 10/2008 | Collins et al. | |
| 2009/0036854 A1 | 2/2009 | Guidotti et al. | |
| 2009/0054760 A1 | 2/2009 | Burke | |
| 2009/0157022 A1 | 6/2009 | MacDonald et al. | |
| 2009/0157032 A1 | 6/2009 | MacDonald et al. | |
| 2009/0204095 A1 | 8/2009 | McDaniel | |
| 2009/0240220 A1 | 9/2009 | MacDonald et al. | |
| 2009/0299312 A1 | 12/2009 | MacDonald et al. | |
| 2009/0326495 A1 | 12/2009 | MacDonald et al. | |
| 2010/0147203 A1 | 6/2010 | MacDonald et al. | |
| 2010/0152642 A1 | 6/2010 | Kim et al. | |
| 2010/0152690 A1 | 6/2010 | Ong et al. | |
| 2010/0152692 A1 | 6/2010 | Ong et al. | |

FOREIGN PATENT DOCUMENTS

| | | |
|---|---|---|
| EM | 000772975-0028 | 11/2008 |
| EP | 0 220 741 A2 | 5/1987 |
| EP | 0 554 565 A1 | 8/1993 |
| EP | 0 557 047 A1 | 8/1993 |
| EP | 0 815 821 A2 | 1/1998 |
| EP | 0 846 454 A1 | 6/1998 |
| EP | 0 910 321 A1 | 4/1999 |
| EP | 1 091 716 A2 | 4/2001 |
| EP | 1 206 923 A1 | 5/2002 |
| GB | 2 244 653 A | 12/1991 |
| GB | D 2 078 590 | 2/1999 |
| JP | 02-107249 A | 4/1990 |
| JP | 03-185197 A | 8/1991 |
| JP | 09-041221 A | 2/1997 |
| JP | 2001-017467 A | 1/2001 |
| JP | 2004-041339 A | 2/2004 |
| JP | 1233575 S | 3/2005 |
| JP | 2006-334113 A | 12/2006 |
| JP | 1318295 S | 12/2007 |
| KR | 10-2006-0114359 A | 11/2006 |
| WO | WO 97/14389 A1 | 4/1997 |
| WO | WO 97/40798 A1 | 11/1997 |
| WO | WO 97/40803 A1 | 11/1997 |
| WO | WO 00/53830 A1 | 9/2000 |
| WO | WO 01/52713 A2 | 7/2001 |
| WO | WO 03/009876 A1 | 2/2003 |
| WO | WO 2005/016103 A1 | 2/2005 |
| WO | WO 2006/021763 A1 | 3/2006 |
| WO | WO 2007/073254 A1 | 6/2007 |
| WO | WO 2007/125352 A1 | 11/2007 |

* cited by examiner

MOISTURE SENSITIVE AUXETIC MATERIAL

BACKGROUND

This invention relates to auxetic materials, in particular, to a material comprising an array of interconnected moisture sensitive auxetic fibers.

Auxetic materials are materials that have a negative or effectively negative Poisson's ratio. In contrast to most conventional materials, auxetic materials possess the property that under a tensile load the material expands perpendicularly to the axis along which the tensile load is applied. In other words, auxetic materials expand as they are stretched. Conversely, materials are also auxetic if a compressive load applied along an axis results in a reduction in the dimension of the material along an axis perpendicular to the axis along which the compressive load is applied. Most materials exhibit a positive Poisson's ratio, this ratio being defined by the ratio of the contractile transverse strain relative to the tensile longitudinal strain.

Prior art auxetic materials are only activated by an applied external force and can essentially be divided into two categories. One category comprises honeycomb like polymeric materials, and the other category comprises materials formed by particles linked by fibrils. However, both of these categories of auxetic materials have significant drawbacks preventing commercialization on an industrial scale. In particular, there are problems in producing such auxetic materials reliably and cost-effectively using techniques which are suitable for commercialization. Recently in order to overcome above problems, a helical fiber was developed. However, the structural characteristics of all prior art auxetic materials made them unsuitable for use in devices or articles that are not exposed to an external force. Thus, what is needed is an auxetic material that not only uses a tensile force to create an auxetic effect and/or pores in the material, but uses a second catalyst for creating an auxetic effect and/or pores in the material.

SUMMARY

One aspect of the present invention is a method of controlling pore size in a porous material including the steps of: providing a material comprising a plurality of interconnected moisture-sensitive auxetic fibers; and applying an aqueous solution to the material so as to create pores in the material in order to produce a desired effect.

In another aspect of the present invention there is an auxetic fiber comprising:

a first component that is a moisture-sensitive shrinkable filament;

a second component that is an elastomeric material, wherein the first component is wrapped about the second component in a helical configuration.

In yet another aspect of the present invention there is an array of auxetic fibers including a first and a second auxetic fiber. Each such fiber includes a first component that is a moisture activated shrinkable filament, and an elastomeric second component. The first component is wrapped about the second component in a helical configuration.

The present invention will now be described in detail with reference to embodiments illustrated in the accompanying drawings.

DETAILED DESCRIPTION

Figure 1:
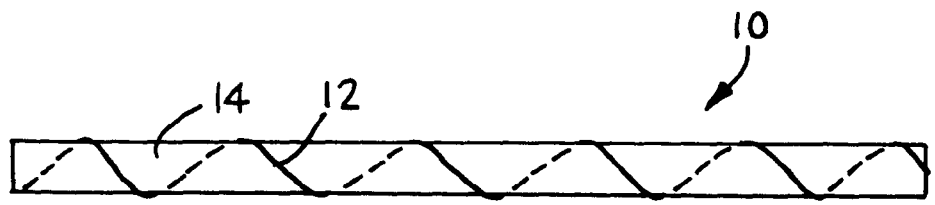
FIG. 1 is a front elevation of a single auxetic fiber of the present invention shown in a dry, unstressed state.

FIG. 1 shows one exemplary embodiment of auxetic fiber 10 in a dry, unstressed state. The fiber 1 0 may be utilized in the production of porous or non-porous materials according to the invention. The auxetic fiber 10 comprises a first component 12 and a second component 14. The first component 12 may be wrapped around the periphery of the second component 14 forming a helix. Desirably, as shown in FIG. 1, the wrapping of the first component 12 around the second component 14 causes no deformation of the second component 14 so that it has a generally linear configuration. The first component is desirably formed from a moisture-sensitive material having a relatively high modulus of elasticity. The second component is preferably formed from a material of lower modulus of elasticity than the first component.

The first component 12 may be a moisture sensitive filament that shrinks (e.g. becomes shorter) when wetted with water, urine, or other water-based liquids. Suitable materials for the first component 12 are liquid shrinkable filaments made from film, fiber, threads, foamed bodies, or the like. Those materials capable of shrinking by 10% or more, or particularly 20% or more when exposed to an aqueous liquid are desirable. Materials such as this include modified cellulose fibers (e.g. cotton and rayon) such as carboxymethylated cotton methylated cotton, ethylated cotton, hydroxyethylated cotton, sulfated cotton, sulfonated cotton, phosphate cotton, cationic cotton, amphoteric cotton, sodium acrylate-, acrylic acid-, acrylnitrile- or acrylamides grafted cellose fiber and crosslinked fiber thereof; wool or silk modified in the same manner as above; modified synthetic fiber, such as partially saponified acylonitrile series of fiber and vinilon fiber which is partially esterfied by maleic acid; and yarns made from these fibers. A desirable material for the first component is a yarn or filament available from Nitivy Company, Japan (SOLVRON Yarn—SHC Grade). This water shrinkable component is a polyvinyl alcohol filament.

Suitable materials for the second component 14 include siloxane, silicone rubber, natural rubber, poly(urethane) and its derivatives, natural rubber, polyisoprene, bytyl rubber and its derivatives, polybutadiene, styrene-butadiene rubber, chloroprene rubber, polychloroprene, neoprene, baypren, ethylene propylene rubber, ethylene propylene diene rubber, epichlorohydrin rubber, polyacrylic rubber, fluorosilicone rubber, fluoroelastomers, perfluoroelastomers, polyether block amides, chlorosulfonated polyethylene, ethylene-vinyl acetate, nitrile rubber or polyamides such as nylon and the like. The material is preferably capable of deformation without fracture. The second component may be an elastic fiber, rod or hollow tube, particularly consisting of a material with an intermediate or a low modulus of elasticity. It should be noted that it is possible for the second component 14 to be formed from a material of relatively high modulus of elasticity, such as nylon, provided it is used in combination with a first component formed from a material of higher modulus of elasticity.

The first component 12 and/or second component 14 may be formed from a continuous material. Preferably, the first component 12 and/or second component 14 are elongate. The first component 12 and/or second component 14 may be at least a hundred times as long as their maximum cross-sectional dimension.

Advantageously, at least one of the first component 12 and the second component 14 is helically wrapped around the other component. The wrapping of the first component 12 around the second component 14 may be in the form of a helix that may have a constant pitch along the second component 14. The pitch may be between zero degrees and ninety degrees relative to the axis.

It will become apparent to the skilled reader that, with a given auxetic fiber of this type, at some applied strains both the first and second components may be helically wrapped around the other component, but at other (higher) applied strains the first component may substantially straighten so as to no longer be helically wrapped around the second component. In principle, the second component might be substantially straight at low applied strain.

The first component may have a diameter that is between 0.01 and 1 times the diameter of the second component. The first component may have a cross-sectional area that is between 0.001 and 1 times the cross-sectional area of the second component.

Figure 2:
FIG. 2 is a front elevation of the fiber shown in FIG. 1 except this fiber is in a wetted state.

FIG. 2 shows the fiber 10 in a wetted state. It is observed that the first component 12 shrinks when exposed to moisture, thereby pulling the second component 14 into a deformed configuration and creating pores. The shrinking first component 12 acts as a pseudo-tensile force that is applied without having to stretch the material. It is noted here that pores may not always be desired. Thus, the material when wetted may only demonstrate a negative Poisson's ratio without pores.

Figure 3:
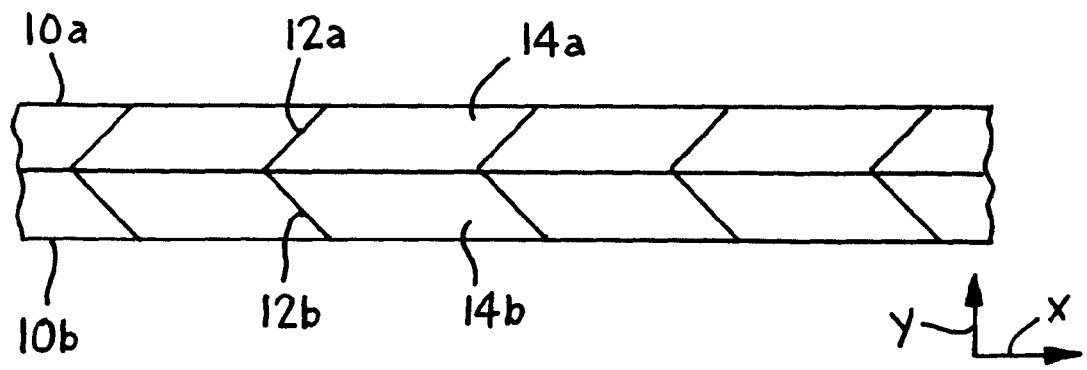
FIG. 3 is a plan view of a material made from the fibers of FIG. 1 with each fiber having a different handedness with respect to adjacent fibers.

FIG. 3 shows a set of auxetic fibers 10 of the type described above with reference to FIG. 1. In particular, it should be noted that the helices formed by the first components 12a, 12b of the auxetic fibers 10a, 10b are in phase and of opposite handedness. It is contemplated that the set of fibers could have the same handedness (not shown).

Figure 4:
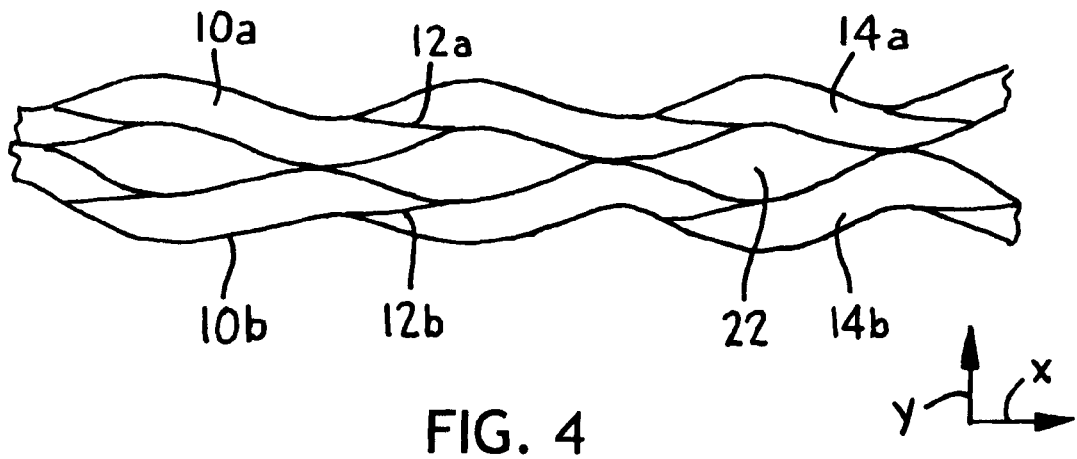
FIG. 4 is a plan view of the material shown in FIG. 3 in a wetted state.

The configuration shown in FIG. 3 depicts the pair of adjacent auxetic fibers in a dry state at a zero tensile load. FIG. 4 depicts the same pair of auxetic fibers 10a, 10b at a loaded state. This load is either due to an external tensile force and/or caused by the wetting and shrinking of the first component 12a, 12b. It can be seen that the result of applying a relatively high tensile load (either by wetting and/or stretching) along the x axis, i.e., along the length of the auxetic fibers, is that the first components 12a, 12b straighten. As a result of the straightening of the first components 12a, 12b, the diameter of the helices formed by the second components 14a, 14b increases. In particular, in the regions 22 in which the pores 20 may be defined, one second component 14a is positively displaced in the y-direction, whereas the other second component 14b is negatively displaced in the y-direction. The effect of the displacements caused by the application of a tensile load is to increase the thickness of the material and possibly to create pores 20. The present invention may utilize this phenomenon to control pore size in porous materials fabricated from auxetic fibers.

Referring still to FIG. 4, when the first components 12a, 12b are wetted, the second components 14a, 14b are deformed. Owing to the helical configuration imposed upon the second components 14a, 14b by the first components 12a, 12b, a similar relationship exists between the second components 14a, 14b, i.e. the helices formed by the second components 14a, 14b are in phase but are of opposite handedness. As a result of this configuration, pores may be formed in regions such as that marked 22, where the helices formed by the second components 14a, 14b are oppositely opposed to the maximum extent.

Figure 5A:
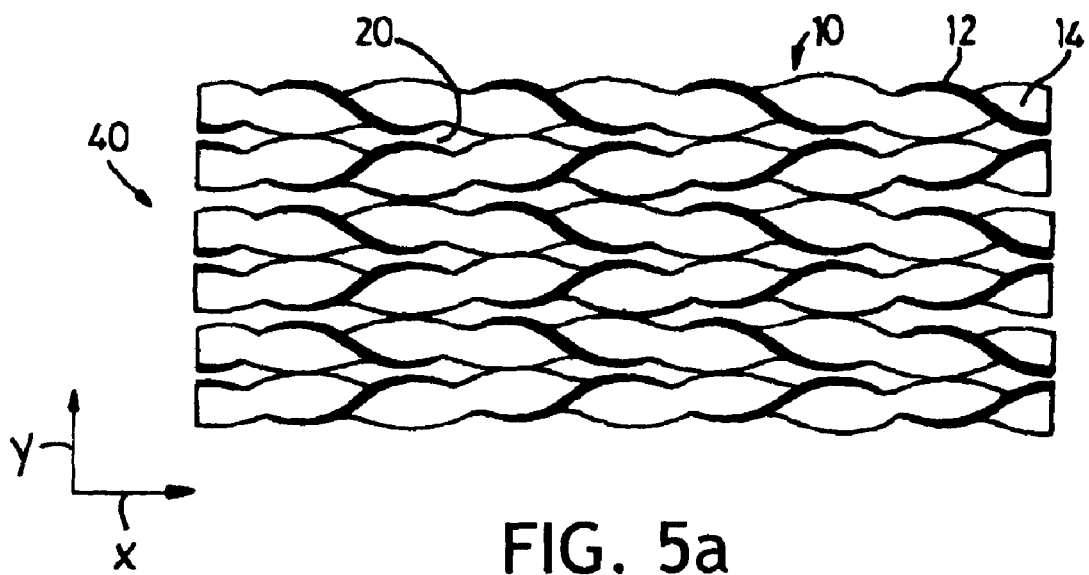
FIG. 5a is the material of FIG. 3, wherein a tensile force has been applied in the X-direction.
Figure 5B:
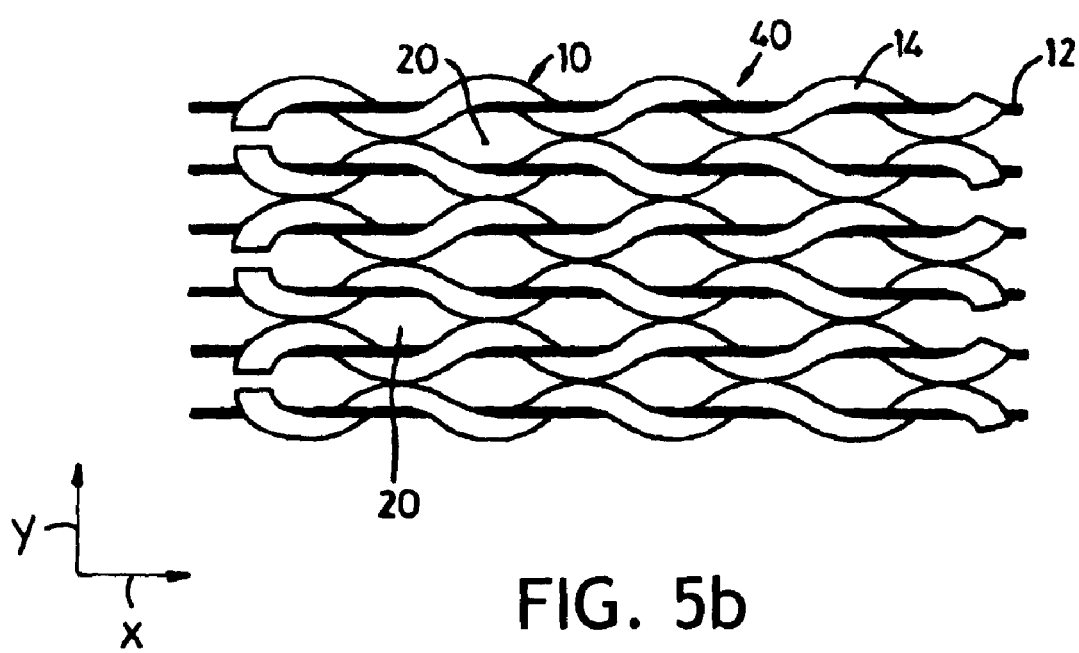
FIG. 5b is the material of FIG. 5b, wherein an additional tensile force has been applied by wetting.

FIGS. 5a and 5b depict a porous material 40. The porous material 40 comprises an array of pairs of adjacent auxetic fibers of the type shown in FIGS. 3 and 4. The array of pairs of auxetic yarns forms a flat sheet fabric. The fabric shown in FIGS. 5a and 5b is a woven fabric, and for reasons of presentational simplicity, these figures depict only the warp fibers. In other words, the weft threads are not shown in FIGS. 5a and 5b, although the skilled reader will appreciate that weft threads will be present in the woven fabric so as to interconnect warp fibers. The weft fibers may be auxetic or non-auxetic in nature. FIG. 5a depicts one embedment of a porous material 40 with a zero tensile load applied along the X-axis. It can be seen that the pores 20 are essentially closed under such conditions. FIG. 5b depicts the porous material 40 having a relatively large tensile load is applied along the x axis causing the fibers 10 to straighten. It is seen that the application of the tensile load causes the pores 20 to open. The load may be caused only by wetting, and/or by an external tensile load.

It is contemplated that the second component 14 could be wrapped around the first component. It is further contemplated that the second component may be in the form of a helix wrapped about a straight first component 12. Also, the pitch of the first component 12 helix may be the same as the pitch of the second component 14 helix.

The auxetic fibers and the material made therefrom have a negative Poisson's ratio. Fibers and/or materials having a Poisson's ratio of between 0 and 35 are preferred. The Poisson's ratio of a fiber is in part dependent on the pitch of the first component. A steep pitch gives rise to a relatively low auxetic effect over a relatively large strain range whereas a shallow pitch gives rise to a relatively large auxetic effect over a relatively narrow strain range.

Figure 6A:
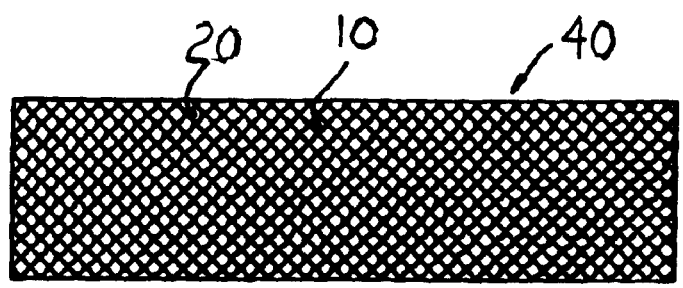
FIG. 6a is an array of fibers such as that shown in FIG. 1, the array in a wetted state to create pores.
Figure 6B:
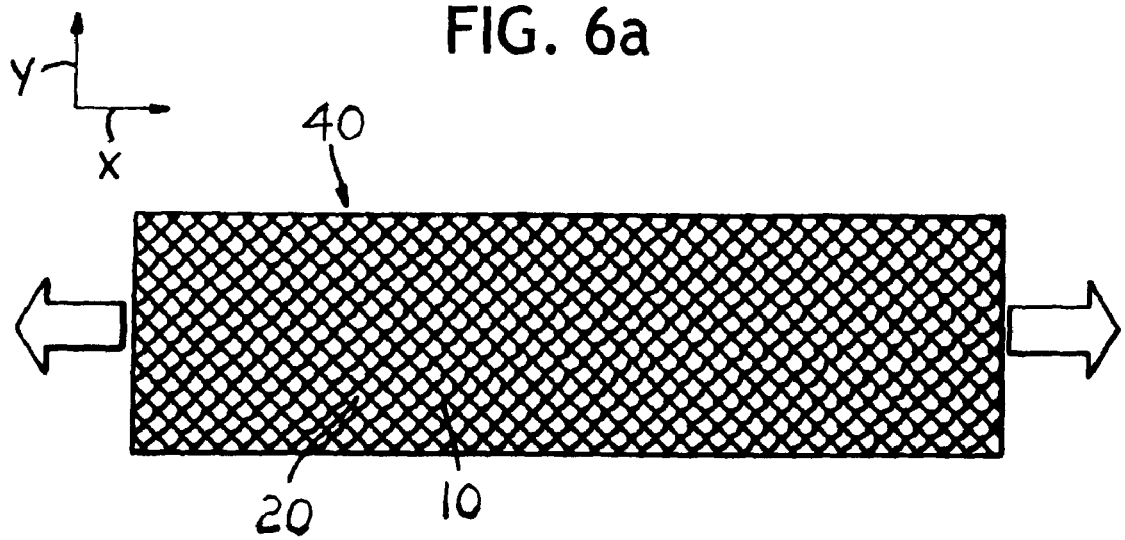
FIG. 6b is an array of fibers such as that shown in FIG. 6 with a tensile force applied in an X-direction to create even larger pores.

FIG. 6a shows a filter material 60 for face masks made from auxetic fibers and defining a plurality of pores 62. FIG. 6a depicts the filter 60 under conditions of low tensile load in the x direction. Under such conditions, the pores 62 are closed or at least of relatively small dimension. FIG. 6b shows the filter 60 under conditions of high tensile load applied along the x axis. Under such conditions of high tensile load, the dimensions of the pores 62 increase, i.e. the pores open up. The tensile load is caused by applying an external force and/or by wetting with an aqueous solution. Thus, by stretching or wetting a filter constructed from appropriately sized auxetic yarns, it is possible to control the pore size. It is contemplated that some applications require an auxetic material that does not develop pores, but simply has a negative Poisson's ratio.

By varying the applied tensile load to the filter material, it is possible to utilize a single filter which is capable of providing a variety of pore sizes. Thus, a single filter can be used in a number of different applications. The invention is not limited to the embodiments and examples provided above. Rather, a wide range of applications can be envisaged in which the pore size of a porous material of the type provided by the invention is controlled for an advantageous purpose. For example, breathable fabrics might be provided having a plurality of pores which open up when a wearer of the fabric undertakes an energetic activity that causes moisture to be released in the form of sweat, thereby causing the pores 62 to open.

The fiber material of the present invention could be used not only for face masks, but for garments where it is desirable to control humidity. Such garments include diapers, incontinence pants, or protective suits. Furthermore, the material could be used as a component in water diapers (e.g. HUGGIES LITTLE SWIMMERS®) to enhance water drainage. Yet another use includes the release of actives as the pores enlarge. For example, if an auxetic fiber is used as a dental floss that contains a healthy ingredient for gums, the floss will release that ingredient during use because it is activated by saliva.

In a further embodiment, the auxetic fibers could be placed into an array that is used for wetness detection. If the auxetic material is layered over an indicator material having a contrasting color or shade, the indicator material will be seen through the auxetic material once it has been wetted and pores have then formed. This application may be useful for wetness detection in a diaper or training pant. Many other uses are possible.

While particular embodiments of the present invention have been illustrated or described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of the invention.

We claim:

1. A method of controlling pore size in a porous material comprising the steps of:
    providing a material comprising a plurality of interconnected moisture-sensitive auxetic fibers; and
    applying an aqueous solution to the material so as to create pores in the material in order to produce a desired effect.

2. A method according to claim 1 in which a tensile force is applied to the material in a longitudinal direction with respect to the auxetic fibers so as to vary the pore size of the material.

3. A method according to claim 1 in which the auxetic fibers comprise a first component and an elastomeric second component.

4. A method according to claim 3 in which the first component and the second component extend generally longitudinally relative to an axis, and a tensile load applied to the first component in part causes the radial position of the second component relative to the axis to vary.

5. A method according to claim 1 in which at least one of the first component and the second component is helically wrapped around the other component.

6. A method according to claim 5 in which pores are formed between adjacent auxetic fibers, wherein helices formed by the first components of the adjacent auxetic fibers are in-phase but of opposite handedness and helices formed by the second components of the adjacent auxetic fibers are in-phase but of opposite handedness.

7. A method according to claim 1 in which the second component comprises a polyvinyl alcohol filament.

8. A method according to claim 1 in which the second component is formed from an elastomeric material.

9. An auxetic fiber comprising:
    a first component comprising a moisture sensitive shrinkable filament;
    a second component having comprising an elastomeric material, wherein the first component is wrapped about the second component in a helical configuration, and wherein the first component comprises polyvinyl alcohol.

10. The auxetic fiber according to claim 9 wherein the second component is straight when in a dry state.

11. The auxetic fiber according to claim 9 wherein the first component has a cross-sectional area that is between 0.001 and 1 times the cross-sectional area of the second component.

12. An array of auxetic fibers comprising:
    a first and a second auxetic fiber each comprising a first component comprising a moisture activated shrinkable filament, and an elastomeric second component, wherein the first component is wrapped about the second component in a helical configuration, and wherein the second component comprises polyvinyl alcohol.

13. The array of claim 12 wherein the first and second auxetic fibers are of opposite handedness.

14. The array of claim 12 wherein the second component is straight when in a dry state.

15. The array of claim 12 wherein the first auxetic fiber and the second auxetic fiber have first component helices that are in phase.

16. The array of claim 12 comprising a woven structure.

* * * * *